(12) United States Patent
Iijima

(10) Patent No.: US 9,376,356 B2
(45) Date of Patent: Jun. 28, 2016

(54) METHOD OR SYSTEM FOR RECOVERING CARBON DIOXIDE

(71) Applicant: MITSUBISHI HEAVY INDUSTRIES, LTD., Tokyo (JP)

(72) Inventor: Masaki Iijima, Tokyo (JP)

(73) Assignee: MITSUBISHI HEAVY INDUSTRIES, LTD., Tokyo (JP)

(*) Notice: Subject to any disclaimer, the term of this patent is extended or adjusted under 35 U.S.C. 154(b) by 0 days.

(21) Appl. No.: 14/760,819

(22) PCT Filed: Feb. 6, 2014

(86) PCT No.: PCT/JP2014/052734
§ 371 (c)(1),
(2) Date: Jul. 14, 2015

(87) PCT Pub. No.: WO2014/125986
PCT Pub. Date: Aug. 21, 2014

(65) Prior Publication Data
US 2015/0353454 A1 Dec. 10, 2015

(30) Foreign Application Priority Data

Feb. 18, 2013 (JP) ................................. 2013-028878

(51) Int. Cl.
| | | |
|---|---|---|
| *C07C 29/151* | (2006.01) | |
| *C10G 3/00* | (2006.01) | |
| *C10L 1/06* | (2006.01) | |
| *C07C 29/152* | (2006.01) | |
| *C01B 3/38* | (2006.01) | |
| *C01B 31/20* | (2006.01) | |
| *C07C 29/80* | (2006.01) | |
| *B01D 53/14* | (2006.01) | |

(52) U.S. Cl.
CPC ........ *C07C 29/1518* (2013.01); *B01D 53/1425* (2013.01); *B01D 53/1475* (2013.01); *C01B 3/38* (2013.01); *C01B 3/384* (2013.01); *C01B 31/20* (2013.01); *C07C 29/152* (2013.01); *C07C 29/80* (2013.01); *C10G 3/49* (2013.01); *C10L 1/06* (2013.01); *B01D 2252/20415* (2013.01); *B01D 2252/20421* (2013.01); *B01D 2252/20484* (2013.01); *B01D 2258/0283* (2013.01); *B01D 2259/65* (2013.01); *C01B 2203/0233* (2013.01); *C01B 2203/0495* (2013.01); *C01B 2203/061* (2013.01); *C01B 2203/0811* (2013.01); *C01B 2203/0883* (2013.01); *C01B 2203/1058* (2013.01); *C01B 2203/1241* (2013.01); *C10L 2200/0492* (2013.01); *C10L 2270/023* (2013.01); *C10L 2290/06* (2013.01); *C10L 2290/12* (2013.01); *C10L 2290/42* (2013.01); *Y02C 10/06* (2013.01); *Y02P 20/129* (2015.11); *Y02P 20/152* (2015.11)

(58) Field of Classification Search
CPC .. C01B 3/52; C01B 31/20; C01B 2203/0233; C01B 2203/06; C01B 2203/061; C01B 2203/062; C01B 2203/0811; C01B 2203/1241; C07C 31/04
USPC .................................................. 518/700, 704
See application file for complete search history.

(56) References Cited

U.S. PATENT DOCUMENTS

| | | | | |
|---|---|---|---|---|
| 4,519,440 A | * | 5/1985 | Weitman | .................... F24J 3/00 165/104.11 |
| 2003/0022948 A1 | | 1/2003 | Seiki et al. | |
| 2006/0248890 A1 | | 11/2006 | Iijima et al. | |

FOREIGN PATENT DOCUMENTS

| | | |
|---|---|---|
| JP | 2003-34503 A | 2/2003 |
| JP | 2006-213580 A | 8/2006 |
| JP | 2011-057485 A | 3/2011 |

OTHER PUBLICATIONS

Notification of Transmittal of Translation of the International Preliminary Report on Patentability (Form PCT/IB/338) issued in counterpart International Application No. PCT/JP2014/052734 mailed Aug. 27, 2015 with Forms PCT/IB/373 and PCT/ISA/237 (5 pages).
International Search Report dated Apr. 1, 2014, issued in corresponding application No. PCT/JP2014/052734 (2 pages).

\* cited by examiner

*Primary Examiner* — Jafar Parsa
(74) *Attorney, Agent, or Firm* — Westerman, Hattori, Daniels & Adrian, LLP

(57) ABSTRACT

A method or system for recovering carbon dioxide is provided with which in a plant for synthesizing methanol from a hydrocarbon gas or synthesizing gasoline therefrom via methanol, the waste heat of a low-temperature reformed gas, which has conventionally been discarded and is difficult to reutilize, can be effectively utilized. In the system for synthesizing methanol or gasoline from a hydrocarbon gas and for recovering carbon dioxide, a reformed gas is produced by steam reforming of the hydrocarbon gas. Since a combustion discharge gas generates when a fuel gas is burned in order to obtain a heat source for the steam reforming, carbon dioxide is recovered from the combustion discharge gas in an absorption tower (40) using an absorption liquid. In a regeneration tower (10), the reformed gas is used first as a heat source for a first reboiler (20A) located at the tower bottom, and the reformed gas having a lowered temperature is then used as a heat source for a second reboiler (20B) located in a middle position to heat the absorption liquid in stages, thereby regenerating the absorption liquid.

14 Claims, 8 Drawing Sheets

METHOD OR SYSTEM FOR RECOVERING CARBON DIOXIDE

TECHNICAL FIELD

The present invention relates to a method or system for recovering carbon dioxide, and particularly relates to a method or system for recovering carbon dioxide in a plant for synthesizing methanol from a hydrocarbon gas or synthesizing gasoline from a hydrocarbon gas via methanol.

BACKGROUND ART

In a conventional plant for synthesizing methanol from a hydrocarbon gas or synthesizing gasoline from a hydrocarbon gas via methanol, there is the problem that uses for waste heat of not greater than approximately 150° C. are limited, and a lot of heat is discarded. In plants for synthesizing methanol or gasoline, measures are taken in which excess steam is introduced when steam-reforming a hydrocarbon gas such as natural gas to prevent carbon deposition during steam reforming. For this reason, a large amount of steam, in addition to hydrogen and carbon monoxide which are primary components of the reformed gas obtained by the steam reforming, remain in the reformed gas. While the reformed gas has high heat of condensation, a lot of the heat is discarded without being used because a lot of steam condenses at temperatures not greater than 150° C.

Japanese Unexamined Patent Application Publication No. 2003-34503A discloses that waste heat is recovered from a reformed gas using a plurality of heat exchangers and effectively used as a heat source of distillation columns that distill methanol. Japanese Unexamined Patent Application Publication No. 2006-213580A discloses that reboilers are configured in multiple stages in a regeneration column of a carbon dioxide absorption liquid, and as the heat source of these multi-stage reboilers, a plurality of steam of different pressures extracted from a turbine is used.

CITATION LIST

Patent Literature

Patent Document 1: Japanese Unexamined Patent Application Publication No. 2003-34503A
Patent Document 2: Japanese Unexamined Patent Application Publication No. 2006-213580A

SUMMARY OF INVENTION

Technical Problem

The present invention takes the above problem into consideration, and an object thereof is to provide a method or system for recovering carbon dioxide in which waste heat of a low-temperature reformed gas, which is difficult to be reutilized and has conventionally been discarded, can be effectively utilized in a plant for synthesizing methanol from a hydrocarbon gas or synthesizing gasoline from a hydrocarbon gas via methanol.

Solution to Problem

To achieve the above object, the present invention is a method for recovering carbon dioxide in a plant for synthesizing methanol from a hydrocarbon gas, includes: a reforming step of producing a reformed gas by a steam reforming reaction of a hydrocarbon gas; a methanol synthesis step of synthesizing methanol from the reformed gas; a combustion step of combusting a fuel gas to obtain a heat source of the steam reforming reaction; a carbon dioxide recovery step of recovering carbon dioxide, using an absorption liquid, from a combustion exhaust gas generated by the combustion; a step of obtaining a plurality of reformed gas heating media or reformed gas and methanol heating media of different temperatures from the reformed gas, or the reformed gas and the methanol; and an absorption liquid regeneration step of regenerating the absorption liquid by heating stepwise the absorption liquid having carbon dioxide absorbed therein to remove carbon dioxide from the absorption liquid, the heating being performed utilizing the plurality of heating media of different temperatures.

Preferably, at least a first heating medium of the plurality of heating media of different temperatures has a temperature of from 115 to 140° C., and a second heating medium has a temperature of from 90 to 110° C.

The method of the present invention may further comprise a distillation step of distilling the methanol synthesized in the methanol synthesis step. In such a method, a heat exchange with the reformed gas generates an additional heating medium of different temperature, and the heating medium is used as a heat source of the distillation.

The method of the present invention may further comprise a gasoline synthesis step of synthesizing gasoline from the methanol synthesized in the methanol synthesis step.

Regeneration of the absorption liquid may be performed by heating stepwise the absorption liquid having carbon dioxide absorbed therein, the heating being performed utilizing the plurality of reformed gases of different temperatures. Alternatively, regeneration of the absorption liquid is performed by heating stepwise the absorption liquid having carbon dioxide absorbed therein, the heating being performed utilizing the reformed gases and methanol of different temperatures.

The present invention, as another aspect, is a system for recovering carbon dioxide and synthesizing methanol from a hydrocarbon gas, includes: a reformer configured to produce a reformed gas by a steam reforming reaction of a hydrocarbon gas; a methanol synthesizing apparatus configured to synthesize methanol from the reformed gas; a combustion apparatus configured to combust fuel gas to obtain a heat source of the steam reforming reaction by the reformer; a carbon dioxide absorption apparatus configured to recover, using an absorption liquid, carbon dioxide from combustion exhaust gas generated by the combustion apparatus; a plurality of heat exchangers configured to use the reformed gas or the reformed gas and the methanol as a plurality of reformed gas heating media or reformed gas and methanol heating media of different temperatures; and an absorption liquid regeneration apparatus configured to regenerate the absorption liquid by heating stepwise the absorption liquid having carbon dioxide absorbed therein by the plurality of heat exchangers to remove carbon dioxide from the absorption liquid, the heating being performed utilizing the plurality of heating media of different temperatures.

Preferably, at least a first heating medium of the plurality of heating media of different temperatures has a temperature of from 115 to 140° C., and a second heating medium has a temperature of from 90 to 110° C.

The system of the present invention may further comprise a distillation apparatus configured to distill the methanol synthesized by the methanol synthesizing apparatus, and an additional heat exchanger configured to obtain an additional heating medium of different temperature by a heat exchange with the reformed gas. In such a system, the additional heating medium of different temperature is used as a heat source of the distillation apparatus.

The system of the present invention may further comprise a gasoline synthesizing apparatus configured to synthesize gasoline from the methanol synthesized by the methanol synthesis apparatus.

The plurality of heat exchangers may be disposed so that the reformed gas and the absorption liquid having carbon dioxide absorbed therein are subjected to a plurality of heat exchanges stepwise. Alternatively, at least a first heat exchanger of the plurality of heat exchangers may be disposed so that the reformed gas and the absorption liquid having carbon dioxide absorbed therein are subjected to a heat exchange, and a second heat exchanger may be disposed so that the methanol and the absorption liquid having carbon dioxide absorbed therein is subjected to a heat exchange.

Advantageous Effects of Invention

Accordingly, with a plurality of heating media of different temperatures obtained from the reformed gas, or the reformed gas and the methanol produced in this system, heating stepwise absorption liquid having carbon dioxide absorbed therein allows the carbon dioxide to be removed from the absorption liquid, so that the absorption liquid can be regenerated; therefore, low-temperature waste heat, which is difficult to be reutilized and has conventionally been discarded, can be effectively utilized.

DESCRIPTION OF EMBODIMENTS

Below, an embodiment of the apparatus and method for recovering carbon dioxide pertaining to the present invention in a methanol synthesis plant or gasoline synthesis plant will be described with reference to the drawings.

Figure 1:
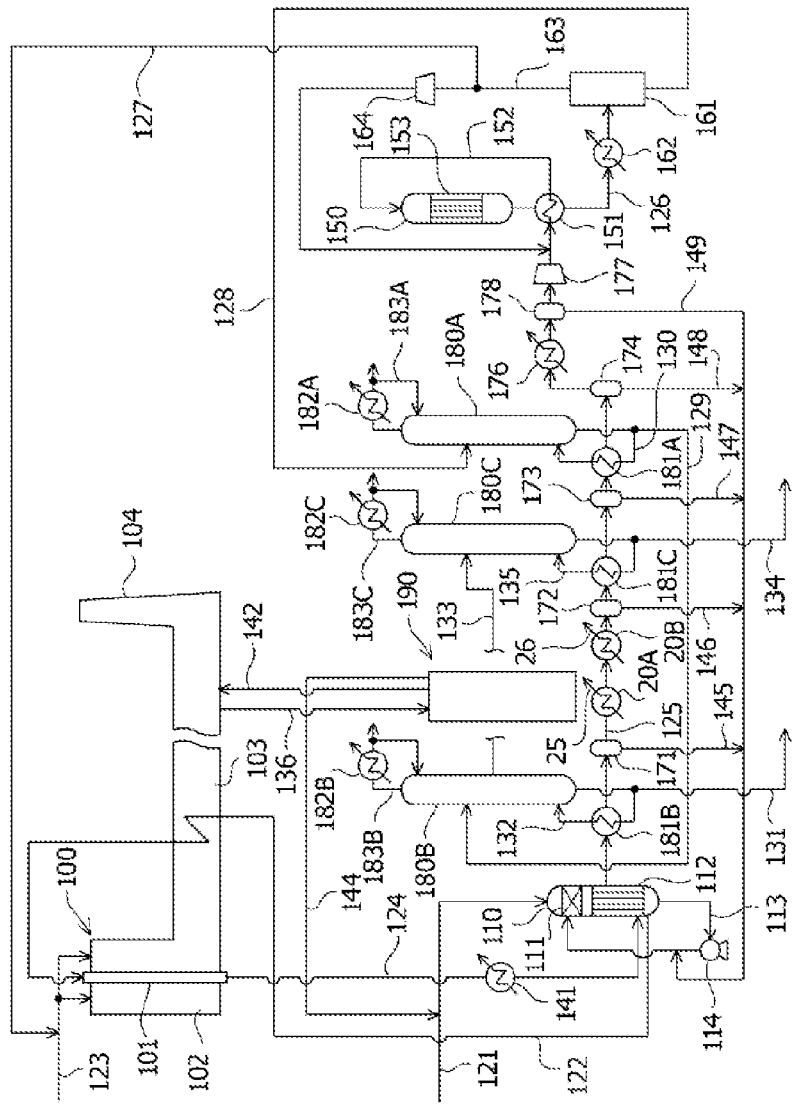
FIG. 1 is a schematic view illustrating an embodiment of a methanol synthesis plant pertaining to the present invention.
Figure 2:
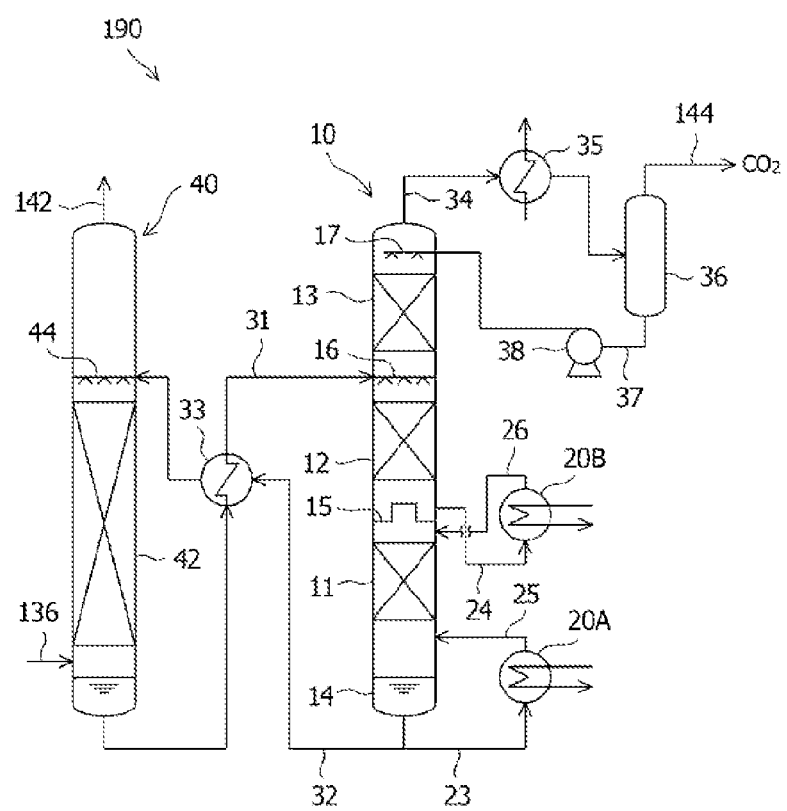
FIG. 2 is a schematic view illustrating a more detailed configuration of the carbon dioxide recovery apparatus illustrated in FIG. 1.

As illustrated in FIG. 1, the methanol synthesis plant of this embodiment primarily includes a reformer 100, which steam-reforms a raw material gas of natural gas (primarily containing a hydrocarbon gas such as methane) and produces a reformed gas primarily containing hydrogen; a methanol synthesis reaction apparatus 150, which synthesizes methanol from the reformed gas thus obtained; a plurality of distillation columns 180 for distilling the methanol obtained by that apparatus; and a carbon dioxide recovery apparatus 190 which recovers carbon dioxide from a combustion exhaust gas generated by the reformer. Moreover, as illustrated in FIG. 2, the carbon dioxide recovery apparatus 190 primarily includes a carbon dioxide recovery column 40, which absorbs and removes carbon dioxide in a combustion exhaust gas by bringing the combustion exhaust gas and a carbon dioxide absorption liquid into gas-liquid contact with each other, and a regeneration column 10, which regenerates the absorption liquid that has absorbed carbon dioxide in the carbon dioxide recovery column.

In the reformer 100, a humidifier 110 for humidifying the raw material gas is provided. The humidifier 110, for example, as illustrated in FIG. 1, is an one-stage heat exchanger-type structure that has a packed layer 111 disposed on the top side thereof, and has a tube 112 disposed on the bottom side, the tube 112 being configured to bring gas and water into contact with each other by the wetted wall method. The humidifier 110 is provided with a recirculating water flow path 113 and a pump 114 for recirculating water from the bottom of the humidifier 110 to the top of the humidifier 110. Moreover, on the top of the humidifier 110 is provided a raw material gas introduction flow path 121 which introduces the raw material gas. According to this humidifier 110, steam can be added to the raw material gas up to substantially saturation pressure at a temperature from 150 to 250° C. Note that the raw material gas introduction flow path 121 may be provided with a desulfurizer (not illustrated), which desulfurizes the raw material gas prior to introduction into the humidifier.

The reformer 100 is connected to the humidifier 110 via a flow path 122 through which the raw material gas that has been humidified by the humidifier 110 flows. The reformer 100 has a reaction pipe 101 for steam-reforming the raw material gas; a combustion radiating part 102 for combusting fuel to heat the reaction pipe 101; a convection part (waste heat recovery part) 103, in which a combustion exhaust gas produced by the combustion radiating part 102 flows; and a chimney 104, which is communicated therewith via the convection part 103. The reaction pipe 101 has a steam reforming catalyst such as a nickel-based catalyst packed therein. A fuel introduction flow path 123 is provided in the combustion radiating part 102 of the reformer 100.

The reaction pipe 101 of the reformer 100 is also connected to the humidifier 110 via a flow path 124 through which a high-temperature reformed gas subjected to steam reforming flows. A heat exchanger 141 is provided in this flow path 124. The humidifier 110 is connected to the methanol synthesis reaction apparatus 150 via a flow path 125 through which this reformed gas flows.

The methanol synthesis reaction apparatus 150 has a preheater 151, which preheats the reformed gas; a recirculation flow path 152 which supplies the reformed gas preheated by the preheater 151 into the apparatus; and a methanol synthesis reactor 153 which performs a methanol synthesis reaction of the reformed gas. This reactor 153 has a methanol synthesis catalyst packed therein.

In the methanol synthesis reaction apparatus 150, a gas-liquid separator 161 is provided via a flow path 126 through which the product of this apparatus flows. This flow path 126 has, in addition to the above-described preheater 151 for preheating the reformed gas, a cooler 162 provided downstream thereof. The gas-liquid separator 161 has a gas recirculation flow path 163, through which separated gas flows, and this flow path 163 is connected to the flow path 125 that is between the preheater 151 and a compressor 177 to be described later. A gas compressor 164 is provided in the gas recirculation flow path 163. Moreover, a purge gas flow path 127 branches off from the gas recirculation flow path 163 between the gas-liquid separator 161 and the gas compressor 164, and is connected to the fuel introduction flow path 123. Additionally, the gas-liquid separator 161 has a flow path 128 which supplies liquid containing primarily separated methanol to a first distillation column 180A among the plurality of distillation columns 180.

The flow path 125 through which the reformed gas flows to the methanol synthesis reaction apparatus 150 is provided with a reboiler (heat exchanger) 181B of a second distillation column 180B, a first condenser 171, a plurality of reboilers (heat exchangers) 20A, 20B of the carbon dioxide recovery apparatus 190, a second condenser 172, a reboiler 181C of a third distillation column 180C, a third condenser 173, a reboiler 181A of the first distillation column 180A, a fourth condenser 174, a cooling heat exchanger 178, a fifth condenser 175, and the compressor 177 in that order from the humidifier 110. In order to utilize the condensed water obtained by the first to fifth condensers 171 to 175 in the humidification of natural gas in the humidifier 110, the first to fifth condensers 171 to 175 are connected to the recirculating water flow path 113 of the humidifier 110 via flow paths 145 to 149.

The flow path 128, through which liquid containing primarily methanol separated by the gas-liquid separator 161 flows, is connected to the first distillation column 180A among the plurality of distillation columns 180. The first distillation column 180A has a first condenser 182A provided near the column top thereof via a recirculation flow path 183A. Moreover, the first distillation column 180A has the bottom thereof connected to the second distillation column 180B via a flow path 129. A first distillation column heating flow path 130 branches off from this flow path 129 near the bottom of the first distillation column 180A, and connects to the lower portion of the first distillation column 180A. The reboiler 181A is provided in this heating flow path 130.

The second distillation column 180B is disposed downstream of the first distillation column 180A via the flow path 129. The second distillation column 180B has a second condenser 182B provided near the column top thereof via a recirculation flow path 183B. The second distillation column 180B has a waste water discharge flow path 131 provided on the bottom thereof. A second distillation column heating flow path 132 branches off from this discharge flow path 131 near the bottom of the second distillation column 180B, and connects near the lower portion of the second distillation column 180B. The above-described reboiler 181B is provided in this heating flow path 132. Moreover, the second distillation column 180B has the vicinity of the column center thereof connected to the third distillation column 180C via a flow path 133.

The third distillation column 180C is disposed downstream of the second distillation column 180B via the flow path 133. The third distillation column 180C has a third condenser 182C provided near the column top thereof via a recirculation flow path 183C. The third distillation column 180C has a waste water discharge flow path 134 provided on the bottom thereof. A third distillation column heating flow path 135 branches off from this discharge flow path 134 near the bottom of the third distillation column 180C, and connects to near the lower portion of the third distillation column 180C. The above-described reboiler 181C is provided in this heating flow path 135.

The carbon dioxide recovery apparatus 190 is connected with the convection part 103 of the reformer 100 via a combustion exhaust gas introduction flow path 136 and a return flow path 142 for exhaust after carbon dioxide has been recovered. Moreover, the carbon dioxide recovery apparatus 190 has the plurality of reboilers 20A, 20B which perform a heat exchange with the flow path 125 through which a high-temperature reformed gas flows. Specifically, as illustrated in FIG. 2, in the carbon dioxide recovery apparatus 190, the combustion exhaust gas introduction flow path 136 is disposed on the column lower portion of the carbon dioxide absorption column 40, and the exhaust gas return flow path 142 is disposed on the column top of the absorption column 40.

The absorption column 40 has an absorption part 42, in which the combustion exhaust gas and the carbon dioxide absorption liquid are brought into gas-liquid contact with each other. The absorption column 40 and the regeneration column 10 are connected by a rich absorption liquid flow path 31, which supplies absorption liquid that has carbon dioxide absorbed therein (hereinafter, called "rich absorption liquid") from the absorption column 40 to the regeneration column 10, and a lean absorption liquid flow path 32, which supplies absorption liquid from which carbon dioxide has been released by the regeneration process in the regeneration column 10 (hereinafter, called "lean absorption liquid") to the absorption column 40. In the rich absorption liquid flow path 31 and the lean absorption liquid flow path 32, a heat exchanger 33, which performs a heat exchange between the rich absorption liquid and the lean absorption liquid, is provided. The absorption column 40 has a plurality of nozzles 44 which spray the lean absorption liquid from the lean absorption liquid flow path 32 into the column.

The carbon dioxide absorption liquid is not particularly limited, but a carbon dioxide absorption liquid primarily containing a basic amine compound is preferred. Examples of the basic amine compound include primary amines containing an alcoholic hydroxy group such as monoethanolamine, 2-amino-2-methine-1-propanol, and the like; secondary amines containing an alcoholic hydroxy group such as diethanolamine, 2-methylamino ethanol, 2-ethylamino ethanol, and the like; tertiary amines containing an alcoholic hydroxy group such as triethanolamine, N-methyldiethanolamine, 2-dimethylamino ethanol, 2-diethylamino ethanol, and the like; polyethylene polyamines such as ethylenediamine, triethylenediamine, diethylenetriamine, and the like; cyclic amines such as piperazines, piperidines, pyrrolidines, and the like; polyamines such as xylylenediamine; and amino acids such as methylamino carboxylic acid. The carbon dioxide absorption liquid may contain one or a plurality of these compounds. The concentration of the basic amine compound may be from 10 to 70% by weight. The carbon dioxide absorption liquid may also contain a carbon dioxide absorption promoter and a corrosion inhibitor, or may contain methanol, polyethylene glycol, sulfolane, and the like as the other medium.

The regeneration column 10, near the center thereof, has a plurality of nozzles 16 which supply the rich absorption liquid from the rich absorption liquid flow path 31 into the column. Moreover, the regeneration column 10 has a plurality of desorption parts for desorbing carbon dioxide from the absorption liquid provided sequentially between the column bottom and the position from which the absorption liquid is supplied. Specifically, a first desorption part 11 is disposed at the column bottom, and a second desorption part 12 is disposed between the column bottom and the position from which the absorption liquid is supplied. A chimney tray 15, which collects down-flowing liquid while allowing rising gas to pass, is provided between the plurality of desorption parts 11, 12.

The regeneration column 10 has a column bottom 14 which collects absorption liquid that flows down inside the column. The lean absorption liquid flow path 32 for supplying lean absorption liquid subjected to regeneration process to the absorption column 40 is provided at this column bottom 14. The regeneration column 10 has a plurality of reboilers 20 which extract some of the lean absorption liquid from inside the column and heat it. As the reboilers 20, the first reboiler 20A disposed on the column bottom 14 and the second reboiler 20B disposed on the chimney tray 15 are provided, as illustrated in FIG. 2. In the first reboiler 20A are provided a first absorption liquid heating flow path 23, which extracts some of the absorption liquid from the column bottom 14 and supplies it to the first reboiler 20A, and a first absorption liquid return flow path 25, which returns the heated absorption liquid to the column lower portion of the regeneration column 10. In the second reboiler 20B are provided a second absorption liquid heating flow path 24, which extracts some of the absorption liquid from the liquid collecting part of the chimney tray 15 and supplies it to the second reboiler 20B, and a second absorption liquid return flow path 26, which returns the heated absorption liquid to the column bottom side of the chimney tray 15.

The plurality of reboilers 20 of the regeneration column 10 are equivalent to the plurality of reboilers disposed in the flow path 125 through which the reformed gas flows, as illustrated in FIG. 1. The first reboiler 20A positioned at the column bottom is positioned on the upstream side in the reformed gas flow path 125, and the second reboiler 20B positioned in the middle of the column is positioned on the downstream side.

Moreover, between the position from which absorption liquid is supplied and the column top, the regeneration column 10 has a water washing part 13, which washes the desorbed carbon dioxide gas. The regeneration column 10 has a carbon dioxide gas discharge flow path 34, which discharges carbon dioxide gas desorbed from the rich absorption liquid from the column top, and this carbon dioxide gas discharge flow path 34 has a condenser 35, which condenses steam that accompanies the carbon dioxide gas, and a separating drum 36, which separates the condensed water thus produced from the gas. In the condenser 35, gas may be cooled using, for example, cooling water. In the separating drum 36, provided is a condensed water return flow path 37 for supplying separated condensed water as washing water of the water washing part 16 of the regeneration column 10. In the condensed water return flow path 37, provided is a pump 38 for sending condensed water to the regeneration column 10.

According to the configuration described above, first, to produce a reformed gas, a combustion fuel such as natural gas, is supplied through the fuel introduction flow path 123 to the combustion radiating part 102 of the reformer 100. Moreover, some of the unreacted gas (purge gas) containing primarily hydrogen to be described later produced by the gas-liquid separator 161 is supplied through the purge gas flow path 127 to the combustion radiating part 102 of the reformer 100. These are combusted together with air, thereby heating the reaction pipe 101 to a temperature sufficient for the reforming reaction (for example, from 850 to 900° C.). The reaction pipe 101 is thus heated because the reforming reaction in the reformer 100 is an endothermic reaction.

The raw material gas (for example, natural gas) primarily containing hydrocarbon is desulfurized as necessary by a desulfurizer (not illustrated), and then supplied through the raw material introduction flow path 121 toward the packed layer 111 at the top of the heat exchanger-type humidifier 110. As for the raw material gas, water is recirculated from the bottom of the humidifier 110 to the top thereof via the recirculating water flow path 113 by operating in advance the pump 114 disposed below the humidifier 110. As a result, the raw material gas supplied to the top of the humidifier 110 is humidified. Specifically, the raw material gas is brought into contact with the water supplied from the recirculating water flow path 113 in the packed layer 111 to be humidified. Then, in the tube 112, the raw material gas is heated and further humidified by heat exchange with the high-temperature reformed gas, which is described later, supplied from the reformer 100 via the flow path 124.

Note that, while the raw material gas is flowing through the raw material gas introduction flow path 121, carbon dioxide recovered by the carbon dioxide recovery apparatus 190 is mixed, as necessary, in a prescribed proportion from a flow path 144. When steam and carbon dioxide are added to natural gas, the molar ratios of methane, steam, and carbon dioxide in the natural gas are preferably set as follows:

Methane ($CH_4$):Steam ($H_2O$)=from 1:1.5 to 1:5
Methane ($CH_4$):Carbon dioxide ($CO_2$)=from 1:0.1 to 1:0.3

The mixed gas of humidified raw material gas and steam is supplied through the flow path 122 into the steam reforming reaction pipe 101 of the reformer 100. Note that the mixed gas that flows through the flow path 122 is preheated when it passes through the convection part 103 of the reformer 100 before being supplied to the reaction pipe 101.

When the mixed gas is supplied to the reaction pipe 101 of the reformer 100, methane, which is the primary component of natural gas, and the steam are steam-reformed in the presence of a catalyst inside the reaction pipe 101, and, as expressed in equations (1) and (2) below, reformed gas containing hydrogen, carbon monoxide, and carbon dioxide is produced.

$$CH_4 + H_2O \rightarrow CO + 3H_2 \tag{1}$$

$$CO + H_2O \rightarrow CO_2 + H_2 \tag{2}$$

Next, to synthesize methanol from this reformed gas, the reformed gas produced by the reformer 100 is supplied to a heat exchanger 41 via the flow path 124. Then, for example, boiler water is heated to generate high-pressure steam, and after the reformed gas itself is cooled, it is supplied to a flow path on the outside of the tube 112 of the humidifier 110. Here, some of the heat of the reformed gas is further recovered and is utilized as a heat source of the humidifier 110.

The reformed gas coming out from the humidifier 110 is supplied through the flow path 125 to the methanol synthesis reaction apparatus 150. At this time, the reformed gas has a temperature of from 180 to 220° C., but in the course of flowing through the flow path 125, it is cooled by heat exchange with the heat exchanger 181B of the second distillation column 180B, the reboilers 20A, 20B of the carbon dioxide recovery apparatus 190, the heat exchanger 181C of the third distillation column 180C, and the heat exchanger 181A of the first distillation column 180A. Additionally, after being cooled by the cooling heat exchanger 178, the reformed gas is pressurized by the compressor 177 to a pressure suitable for the methanol synthesis reaction (for example, from 50 to 150 atm).

Among the reboilers 20 of the carbon dioxide recovery apparatus, in the first reboiler 20A on the upstream side, high-temperature reformed gas having a temperature of, for example, from 115 to 140° C. can be obtained as a heating medium, and in the second reboiler 20B on the downstream side, low-temperature reformed gas having a temperature of, for example, from 90 to 110° C. can be obtained as a heating medium. In this manner, the waste heat of the reformed gas is effectively utilized by the reboiler 181 of the distillation column 180 and the reboilers 20 of the carbon dioxide recovery apparatus, and the reformed gas itself is cooled. Moreover, the steam contained in the reformed gas is condensed by the first to fifth condensers 171 to 175, and the produced condensed water is supplied through the flow paths 145 to 149 to the recirculating water flow path 113 of the humidifier 110, and is used to humidify the raw material gas in the humidifier 110.

The reformed gas pressurized by the compressor 177 is supplied through the flow path 125 to the preheater 151 of the methanol synthesis reaction apparatus 150, and is preheated to a temperature suitable for the methanol synthesis reaction (for example, from 200 to 300° C.). Then, the reformed gas is supplied through the recirculation flow path 152 to the reactor 153 packed with the methanol synthesis catalyst. Note that unreacted gas separated by the gas-liquid separator 161 is supplied through the gas recirculation flow path 163 to the flow path 125 between the compressor 177 and the preheater 151, and mixes with the reformed gas. In the reactor 153, a product containing methanol and water is obtained by the methanol synthesis reaction, as expressed in equations (3) and (4) below.

$$CO + 2H_2 \rightarrow CH_3OH \tag{3}$$

$$CO_2 + 3H_2 \rightarrow CH_3OH + H_2O \tag{4}$$

Moreover, in the methanol synthesis reaction, impurities such as dimethyl ether and ethanol are produced as by-products. The product obtained in the reactor 153 contains these impurities, water, unreacted hydrogen, and the like, together with methanol. This substance that contains a lot of components other than methanol is called crude methanol.

The crude methanol from the reactor 153 is sequentially supplied through the recirculation flow path 152 and flow path 126 to the cooler 162, and is cooled to substantially room temperature. At this time, almost all of the methanol and water in the crude methanol is condensed and becomes liquid, which flows into the gas-liquid separator 161. In the gas-liquid separator 161, it is separated into unreacted gas primarily containing hydrogen (hydrogen-rich unreacted gas) and liquid crude methanol.

This hydrogen-rich unreacted gas is sent through the gas recirculation flow path 163 to the gas compressor 164. Then, after being pressurized, the hydrogen-rich unreacted gas is supplied through the gas recirculation flow path 163 to the reactor 153 together with the reformed gas, as described above. Some of the hydrogen-rich unreacted gas is utilized as some of the fuel of the combustion radiating part 102 of the reformer 100 via the purge gas flow path 127 as purge gas.

The liquid crude methanol separated by the gas-liquid separator 161 is supplied to the first distillation column 180A via the flow path 128, and this liquid crude methanol is heated utilizing heat of the reboiler 181A disposed in the reformed gas flow path 125. Low-boiling-point organic compounds in the crude methanol are concentrated in the column top of the first distillation column 180A and are partially condensed and refluxed in the first condenser 182A, and the remainder is discharged to outside the system together with dissolved gas.

The bottom of the first distillation column 180A has primarily methanol and water, which are supplied to the second distillation column 180B via the flow path 129. This methanol and water supplied to the second distillation column 180B are heated utilizing heat of the reboiler 181B disposed in the high-temperature reformed gas flow path 125. In the column top of the second distillation column 180B, the methanol fraction is cooled by the second condenser 182B to be condensed, and by reflux, the methanol is purified to high purity and drawn to outside the system. The bottom of the second distillation column 180B has primarily water which contains the small amount of high-boiling-point organic compounds and organic acids, and the trace amount of inorganic matter produced by the apparatus. This waste water is discharged to outside the system via the flow path 131 from the bottom of the second distillation column 180B.

Near the center of the second distillation column 180B, liquid containing primarily unpurified methanol is present, and this liquid is supplied to the third distillation column 180C via the flow path 133. This liquid supplied to the third distillation column 180C is heated utilizing heat of the reboiler 181C disposed in the reformed gas flow path 125. In the column top of the third distillation column 180C, the methanol fraction is cooled by the third condenser 182C to be condensed, and by reflux, the methanol is purified to high purity and drawn to outside the system. Waste water containing primarily water is collected in the bottom of the third distillation column 180C, and this waste water is discharged to outside the system from the bottom of the third distillation column 180C via the flow path 134.

Next, recovery of carbon dioxide in the carbon dioxide absorption apparatus 190 will be described. The combustion exhaust gas containing carbon dioxide produced in the combustion radiating part 102 is cooled while passing through the convection part 103 by heat exchange with natural gas to which steam and the like has been added, which flows through the raw material gas introduction flow path 122. The cooled combustion exhaust gas is supplied through the combustion exhaust gas introduction flow path 136 to the absorption column 40 of the carbon dioxide recovery apparatus 190. Additionally, in the absorption column 40, absorption liquid is supplied from the nozzles 44 disposed on the tip of the lean absorption liquid flow path 32. In the absorption part 42, the combustion exhaust gas and the absorption liquid are brought into gas-liquid contact with each other, and the carbon dioxide in the gas is absorbed by the absorption liquid. The combustion exhaust gas from which carbon dioxide has been removed is returned through the exhaust gas flow path 142 to the convection part 103 of the reformer 100, and discharged to the outside from the chimney 104.

As illustrated in FIG. 2, the rich absorption liquid which has absorbed carbon dioxide in the absorption column 40 is discharged via the rich absorption liquid flow path 31, and after being heated by lean absorption liquid in the heat exchanger 33, is sent to the regeneration column 10. In the regeneration column 10, the rich absorption liquid is sprayed onto the second desorption part 12 from the nozzles 16 disposed on the tip of the rich absorption liquid flow path 31. The rich absorption liquid is heated and partially releases carbon dioxide while it flows down the second desorption part 12, and is collected in the liquid collecting part of the chimney tray 15. Then, the rich absorption liquid collected in the liquid collecting part is sent to the second reboiler 20B via the second absorption liquid heating flow path 24, and is heated by a heating medium of low-temperature reformed gas having a temperature of, for example, from 90 to 110° C. Then, the rich absorption liquid is returned to the column bottom side of the chimney tray 15 of the regeneration column 10 via the second absorption liquid return flow path 26.

The returned rich absorption liquid is heated while it flows down the first desorption part 11 positioned on the column bottom side of the chimney tray 15, and flows down to the column bottom 14 while partially releasing carbon dioxide. The absorption liquid collected in the column bottom 14 is sent to the first reboiler 20A via the first absorption liquid heating flow path 23, and is heated by a heating medium of high-temperature reformed gas having a temperature of, for example, from 115 to 140° C. Then, the absorption liquid is returned to the column lower portion of the regeneration column 10 via the first absorption liquid return flow path 25. In this manner, all of the carbon dioxide remaining in the column bottom 14 is released and the absorption liquid can be regenerated with heating media having different temperatures so as to achieve a temperature gradient in which the reboiler on the column bottom side has the highest temperature among the plurality of reboilers 20. The regenerated lean absorption liquid is supplied from the column bottom 14 via the lean absorption liquid flow path 32 to the absorption column 40 after the heat exchanger 33 heats the rich absorption liquid to recover the heat.

The carbon dioxide desorbed from the rich absorption liquid passes through the first desorption part 11, the chimney tray 15, and the second desorption part 12, and then rises to the water washing part 13. In the water washing part 13, washing water is sprayed from a plurality of nozzles 17 provided on the tip of the condensed water return flow path 37, and the absorption liquid that accompanies the carbon dioxide gas is removed. The carbon dioxide gas washed in the water washing part 13 is discharged from the carbon dioxide gas discharge flow path 34 provided on the column top of the regeneration column 10.

In the carbon dioxide gas discharge flow path 24, first, steam that accompanies the carbon dioxide gas is condensed by the condenser 25, and additionally, this condensed water is separated by the separating drum 36. The separated condensed water is returned to the regeneration column 10 via the condensed water return flow path 37 by the pump 38. The carbon dioxide gas from which condensed water has been removed is supplied through the flow path 144 to the flow path 121 through which the raw material gas flows, and can be added to the raw material gas (methane).

In this manner, of the heat of condensation of the reformed gas which is a heating medium, low-temperature waste heat, which is difficult to be reutilized and has conventionally been discarded, can be effectively utilized in the first reboiler 20A at the column bottom by utilizing high-temperature reformed gas produced by the reformer 100 as a heat source of the absorption liquid regeneration column 10, and by further utilizing the waste heat utilized in this first reboiler 20A as a heat source of the second reboiler 20B disposed in the middle of the column.

One embodiment of the present invention has been described using FIGS. 1 and 2, but the present invention is not limited thereto, and the arrangement of the reboilers for the distillation columns and the reboilers of the regeneration column provided in the flow path 125 through which a reformed gas flows may be configured as follows.

Figure 3:
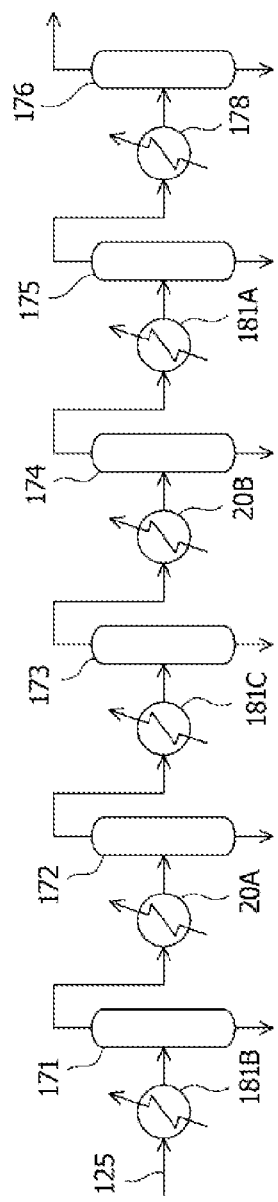
FIG. 3 is a schematic view illustrating another arrangement of the heat exchangers and condensers in the flow path of reformed gas illustrated in FIG. 1.

In the embodiment illustrated in FIG. 3, in the flow path 125 through which the reformed gas flows, the reboiler 181B of the second distillation column, the first condenser 171, the first reboiler 20A of the regeneration column, the second condenser 172, the reboiler 181C of the third distillation column 180C, the third condenser 173, the second reboiler 20B of the regeneration column, the fourth condenser 174, the reboiler 181A of the first distillation column 180A (for methanol gas extraction), a fifth condenser 175, the cooling heat exchanger 178, and a sixth condenser 176 may be provided in that order from the reformer. In this manner, a plurality of reboilers of the regeneration column do not have to be disposed continuously in the reformed gas flow path 125, and heat exchangers or reboilers for other applications may be disposed therebetween, and may be disposed in positions so that the reformed gas having the temperature gradient required in each of the plurality of reboilers of the regeneration column can be obtained.

Figure 4:
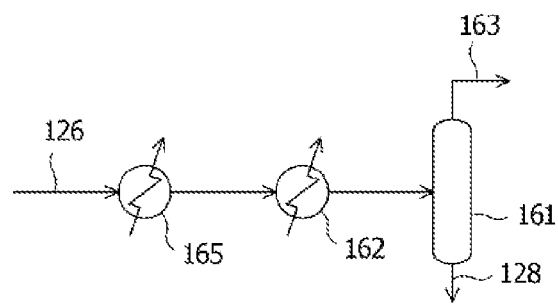
FIG. 4 is a schematic view illustrating another arrangement of the flow path of methanol product illustrated in FIG. 1.

In the embodiment illustrated in FIG. 3, a heat exchanger for preheating boiler supply water 165 is preferably provided at a position between the preheater 151 and the cooler 162 in the flow path 126 which supplies the product obtained in the methanol synthesis reaction apparatus 150 to the gas-liquid separator 161, as illustrated in FIG. 4. Because the product from the methanol synthesis reaction apparatus 150 has a temperature of, for example, from 120 to 140° C. even after passing through the preheater 151, it is possible to obtain steam having a temperature of from 100 to 120° C. in the heat exchanger for preheating boiler supply water 165.

In the embodiments illustrated in FIGS. 1 to 4, a configuration in which carbon dioxide is recovered from the combustion exhaust gas of the carbon dioxide recovery apparatus 190 in order to add the carbon dioxide to the raw material gas (methane) which undergoes steam forming in the reformer 100 has been described, but the present invention is not limited thereto. For example, the present invention may be configured so that all carbon dioxide contained in the combustion exhaust gas is recovered in the carbon dioxide recovery apparatus 190, and is then introduced into a plurality of compressors (not illustrated) and utilized separately as compressed carbon dioxide. The arrangements of the reboilers of the regeneration column and the reboilers of the distillation columns in this case are illustrated in FIGS. 5 and 6.

Figure 5:
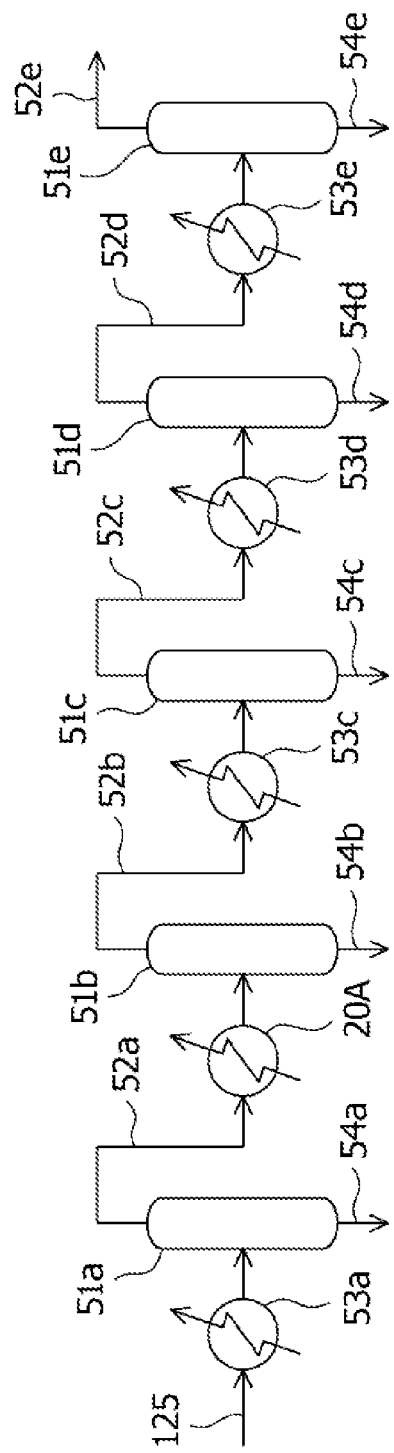
FIG. 5 is a schematic view illustrating yet another arrangement of the heat exchangers and condensers in the flow path of reformed gas.
Figure 6:
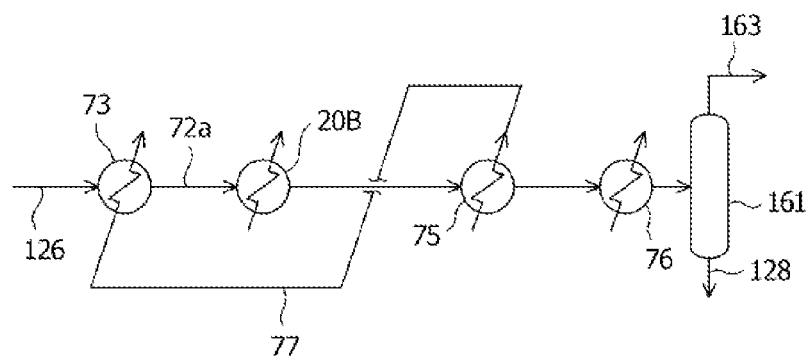
FIG. 6 is a schematic view illustrating yet another arrangement of the heat exchangers in the flow path of methanol product.

As illustrated in FIG. 5, in the flow path 125 through which the reformed gas flows, a reboiler 53a of the second distillation column, a first condenser 51a, a first reboiler 20A53b of the regeneration column, a second condenser 51b, a reboiler 53c of the third distillation column, a third condenser 51c, a reboiler 53d of the first distillation column (for methanol gas extraction), a fourth condenser 51d, a cooling heat exchanger 53e, and a fifth condenser 51e may be provided in that order from the reformer. Moreover, as illustrated in FIG. 6, in the flow path 126 of the product obtained in the methanol synthesis reaction apparatus, a second heat exchanger 73 for preheating boiler supply water, the second reboiler 20B of the regeneration column, a first heat exchanger for preheating boiler supply water 75, and a cooler 76 are provided in that order from the preheater of the methanol synthesis reaction apparatus. Between the first heat exchanger for preheating boiler supply water 75 and the second heat exchanger 73, a steam flow path 77 which supplies steam heated by the first heat exchanger 75 to the second heat exchanger 73 is provided.

In this manner, when the amount of carbon dioxide recovered from the combustion exhaust gas in the carbon dioxide recovery apparatus 190 increases, the energy required in the plurality of boilers 20 of the regeneration column 10 cannot be provided only by the waste heat of the flow path 125 through which reformed gas flows. Therefore, of the plurality of reboilers of the regeneration column, the first reboiler 20A positioned at the column bottom is disposed in the reformed gas flow path 125, and the second reboiler 20B positioned in the middle of the column is disposed in the methane product flow path 126. In the first reboiler 20A, a heating medium of high-temperature reformed gas having a temperature of, for example, from 115 to 140° C. can be obtained. Moreover, in the second reboiler 20B, a heating medium of low-temperature methanol product having a temperature of, for example, from 90 to 110° C. can be obtained. Additionally, steam having a temperature of from 80 to 100° C. can be obtained in the first heat exchanger for preheating boiler supply water 75, and the steam is further supplied to the second heat exchanger 73 via the steam flow path 77, steam having a temperature of from 100 to 120° C. can be obtained. In such a configuration, it is possible to obtain heating media of reformed gas and methanol product having a temperature gradient required in each of the plurality of boilers of the regeneration column.

Moreover, in the embodiments illustrated in FIGS. 1 to 6, a configuration in which a product obtained in the methanol synthesis reaction apparatus 150 undergoes methanol distillation by a plurality of distillation columns 180 has been described, but the present invention is not limited thereto. For example, the present invention may also be configured so that the product obtained in the methanol synthesis reaction apparatus 150 is supplied to a gasoline synthesis reaction apparatus (not illustrated) without being distilled, and gasoline is synthesized from methanol. In the gasoline synthesis reaction apparatus, gasoline can be synthesized from methanol as expressed in equations (5) and (6) below.

$$2CH_3OH \rightarrow CH_3OCH_3 + H_2O \quad (5)$$

$$\tfrac{1}{2}nCH_3OCH_3 \rightarrow (CH_2)n + \tfrac{1}{2}nH_2O \quad (6)$$

In this manner, methanol becomes gasoline by the gasoline synthesis reaction expressed in equation (6) via the dimethyl ether (DME) synthesis reaction expressed in equation (5). In the gasoline synthesis reaction apparatus, two types of catalyst—a DME synthesis catalyst and a gasoline synthesis catalyst—are provided in two stages, and the two reactions can proceed in a stage-wise manner. The DME synthesis catalyst may be, for example, a known catalyst such as an aluminosilicate zeolite catalyst or the like. The gasoline synthesis catalyst may also be a known catalyst such as an aluminosilicate zeolite catalyst or the like. The arrangement of the reboilers of the regeneration column provided in the flow path 125 through which the reformed gas flows in this case is illustrated in FIG. 7.

Figure 7:
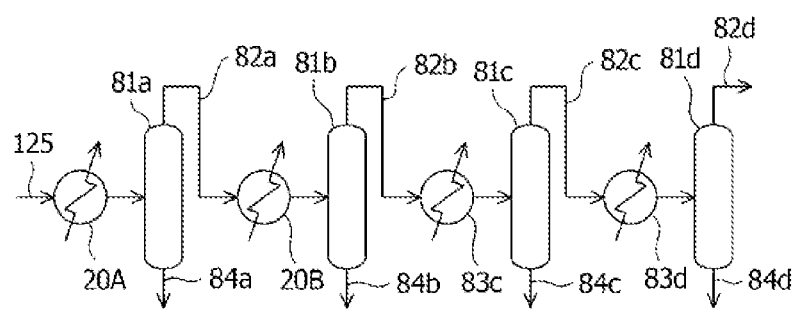
FIG. 7 is a schematic view illustrating an arrangement of heat exchangers and condensers in the flow path of reformed gas in a gasoline synthesis plant.

As illustrated in FIG. 7, in the flow path 125 through which the reformed gas flows, the first reboiler 20A of the regeneration column, a first condenser 81a, the second reboiler 20B of the regeneration column, a second condenser 81b, a reboiler 83c of the distillation column (for methanol gas extraction), a third condenser 81c, a cooling heat exchanger 83d, and a fourth condenser 81d, 53e may be provided in that order from the reformer. Note that the configuration in the flow path 126 of the product obtained by the methanol synthesis reaction apparatus is the same as that of FIG. 4. In addition, the carbon dioxide recovery apparatus 190 has a configuration in which all carbon dioxide gas is recovered from the combustion exhaust gas.

According to such a configuration, even when the amount of carbon dioxide recovered in the carbon dioxide recovery apparatus 190 increases, crude methanol produced in the distillation columns can be supplied to the gasoline synthesis reaction apparatus without being distilled, and therefore, the energy required in the plurality of boilers 20 of the regeneration column 10 can be provided by waste heat of the flow path 125 through which the reformed gas flows. In the first reboiler 20A, high-temperature reformed gas having a temperature of, for example, from 115 to 140° C. can be obtained as a heating medium. In the second reboiler 20B, low-temperature reformed gas having a temperature of, for example, from 90 to 110° C. can be obtained as a heating medium. Therefore, it is possible to obtain heating media having a temperature gradient required in each of the plurality of boilers of the regeneration column.

EXAMPLES

A simulation of the heat energy balance in methanol synthesis and carbon dioxide recovery in the configuration illustrated in FIGS. 3 and 4 was performed (Working Example 1). Moreover, a simulation of the heat energy balance in methanol synthesis and carbon dioxide recovery in the configuration illustrated in FIGS. 5 and 6 was performed (Working Example 2). Additionally, a simulation of the heat energy balance in gasoline synthesis and carbon dioxide recovery in the configuration illustrated in FIGS. 7 and 4 was performed (Working Example 3).

Figure 8:
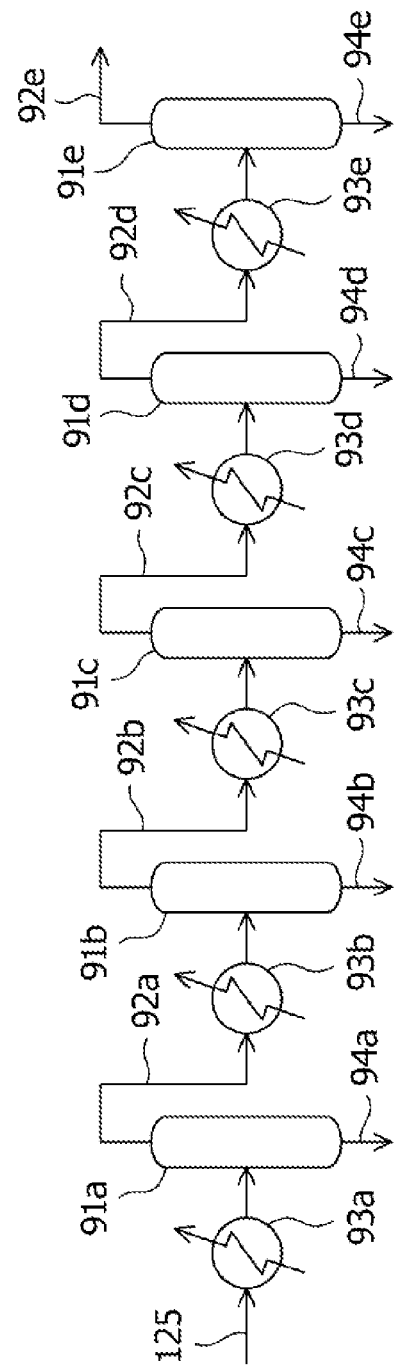
FIG. 8 is a schematic view illustrating an arrangement of a comparative example of heat exchangers and condensers in the flow path of reformed gas.
Figure 9:
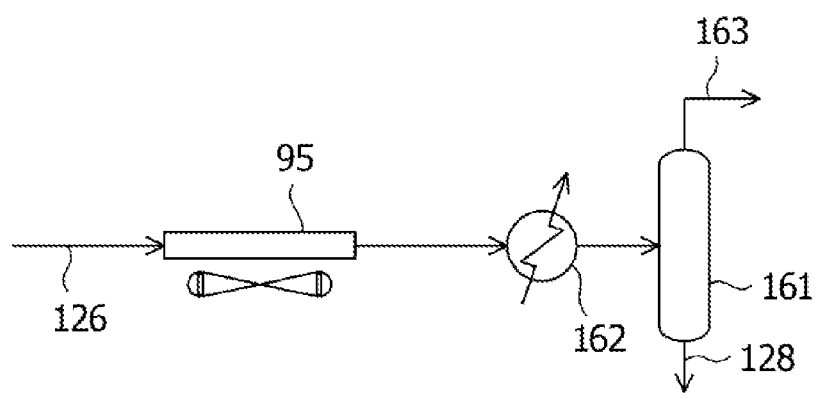
FIG. 9 is a schematic view illustrating a conventional arrangement of heat exchangers in the flow path of methanol product.

Note that, for comparison, a simulation of the heat energy balance in methanol synthesis when carbon dioxide is not recovered was performed (Comparative Example 1). The arrangement of the reformed gas flow path of Comparative Example 1 is illustrated in FIG. 8, and the arrangement of the methanol product flow path is illustrated in FIG. 9. As illustrated in FIG. 8, in the reformed gas flow path 125, a reboiler 93a of a second distillation column, a reboiler 93b of a third distillation column, a reboiler 93c of a first distillation column, a heat exchanger for preheating boiler supply water 93d, and a cooling heat exchanger 93e are arranged in order from the reformer. Moreover, as illustrated in FIG. 9, in the methanol product flow path 126, an air cooler 95 is disposed on the upstream side of the cooler 162.

Various conditions include, in each of the reboilers and heat exchangers of Working Example 1, the temperature (° C.) of the reformed gas or methanol product (heating medium) after being subjected to heat exchange by the reboiler or heat exchanger, the temperature (° C.) of the heated matter heated by the reboiler or heat exchanger, and the calorific value (kcal/h) obtained in the reboiler or heat exchanger are shown in Table 1. In addition, the flow rates of the condensed water discharged from the first to sixth condensers 171 to 176 are shown in Table 2. Similarly, various conditions of Working Example 2 are shown in Tables 3 and 4, various conditions of Working Example 3 are shown in Tables 5 and 6, and various conditions of Comparative Example 1 are shown in Tables 7 and 8. Note that the reformed gas initially had a temperature of 200° C. and a pressure of 18.1 kg/cm$^2$G, which is common to Working Examples 1 to 3 and Comparative Example 1. Similarly, the methanol product initially had a temperature of 129° C. and a pressure of 96 kg/cm$^2$ G, which is also common to those examples. The simulation results are shown in Table 9.

TABLE 1

|  | Temperature of heating medium after heat exchange (° C.) | Temperature of heated matter (° C.) | Calorific value (kcal/h) |
|---|---|---|---|
| Reboiler of second distillation column (181B) | 155 | 142 | 14.0 × 10$^6$ |
| First reboiler of regeneration column (20A) | 147 | 120 | 15.9 × 10$^6$ |
| Reboiler of third distillation column (181C) | 137 | 115 | 14.2 × 10$^6$ |
| Second reboiler of regeneration column (20B) | 124 | 100 | 11.3 × 10$^6$ |
| Reboiler of first distillation column (181A) | 101 | 83 | 15.9 × 10$^6$ |

TABLE 1-continued

| | Temperature of heating medium after heat exchange (° C.) | Temperature of heated matter (° C.) | Calorific value (kcal/h) |
|---|---|---|---|
| Cooling heat exchanger (178) | 39 | — | $16.0 \times 10^6$ |
| Heat exchanger for preheating boiler supply water (165) | 107 | 108 | $17.0 \times 10^6$ |
| Cooler (162) | 45 | — | $38.3 \times 10^6$ |

TABLE 2

| | Discharge water flow rate (ton/h) |
|---|---|
| First condenser (171) | 12.9 |
| Second condenser (172) | 27.9 |
| Third condenser (173) | 25.8 |
| Fourth condenser (174) | 19.0 |
| Fifth condenser (175) | 26.0 |
| Sixth condenser (176) | 12.8 |

TABLE 3

| | Temperature of heating medium after heat exchange (° C.) | Temperature of heated matter (° C.) | Calorific value (kcal/h) |
|---|---|---|---|
| Reboiler of second distillation column (53a) | 155 | 142 | $14.0 \times 10^6$ |
| First reboiler of regeneration column (20A) | 137 | 120 | $30.1 \times 10^6$ |
| Reboiler of third distillation column (53c) | 121 | 115 | $14.2 \times 10^6$ |
| Reboiler of first distillation column (53d) | 98 | 83 | $15.9 \times 10^6$ |
| Cooling heat exchanger (53e) | 39 | — | $13.1 \times 10^6$ |
| First heat exchanger for preheating boiler supply water (73) | 126 | 108 | $2.2 \times 10^6$ |
| Second reboiler of regeneration column (20B) | | 105 | $12.5 \times 10^6$ |
| Second heat exchanger for preheating boiler supply water (75) | 100 | 100 | $14.8 \times 10^6$ |
| Cooler (76) | 45 | — | $\times 10^6$ |

TABLE 4

| | Discharge water flow rate (ton/h) |
|---|---|
| First condenser (51a) | 12.9 |
| Second condenser (51b) | 83.7 |
| Third condenser (51c) | 23.4 |
| Fourth condenser (51d) | 19.4 |
| Fifth condenser (51e) | 15.0 |

TABLE 5

| | Temperature of heating medium after heat exchange (° C.) | Temperature of heated matter (° C.) | Calorific value (kcal/h) |
|---|---|---|---|
| First reboiler of regeneration column (20A) | 137 | 120 | $44.1 \times 10^6$ |
| Second reboiler of regeneration column (20B) | 122 | 105 | $13.7 \times 10^6$ |
| Reboiler of distillation column (83c) | 104 | 83 | $15.9 \times 10^6$ |
| Cooling heat exchanger (83d) | 39 | — | $13.6 \times 10^6$ |
| Heat exchanger for preheating boiler supply water (165) | 107 | 108 | $17.0 \times 10^6$ |
| Cooler (162) | 45 | — | $38.3 \times 10^6$ |

TABLE 6

| | Discharge water flow rate (ton/h) |
|---|---|
| First condenser (81a) | 66.6 |
| Second condenser (81b) | 22.0 |
| Third condenser (81c) | 26.0 |
| Fourth condenser (81d) | 9.8 |

TABLE 7

| | Temperature of heating medium after heat exchange (° C.) | Temperature of heated matter (° C.) | Calorific value (kcal/h) |
|---|---|---|---|
| Reboiler of second distillation column (93a) | 155 | 142 | $14.0 \times 10^6$ |
| Reboiler of third distillation column (93b) | 148 | 115 | $14.2 \times 10^6$ |
| Reboiler of first distillation column (93c) | 137 | 83 | $15.9 \times 10^6$ |
| Heat exchanger for preheating boiler supply water (93d) | 118 | 108 | $17.0 \times 10^6$ |
| Cooling heat exchanger (93e) | 39 | — | $26.2 \times 10^6$ |
| Air cooler (95) | 71 | — | $44.5 \times 10^6$ |
| Cooler (162) | 45 | — | $12.5 \times 10^6$ |

TABLE 8

| | Discharge water flow rate (ton/h) |
|---|---|
| First condenser (91a) | 12.9 |
| Second condenser (91b) | 25.8 |
| Third condenser (91c) | 27.9 |
| Fourth condenser (91d) | 27.8 |
| Fifth condenser (91e) | 30.0 |

TABLE 9

| | Working Example 1 | Working Example 2 | Working Example 3 | Comparative Example 1 |
|---|---|---|---|---|
| Carbon dioxide recovery rate (ton/d) | 34.4 | 73.2 | 73.2 | — |
| Carbon dioxide recovery reboiler calorific value (kcal/h) | $27.2 \times 10^6$ | $57.8 \times 10^6$ | $57.8 \times 10^6$ | — |

In all of the results of Working Examples 1 to 3 as shown in Table 9, the calorific value of the reboilers necessary to recover carbon dioxide can be provided by waste heat generated in a methanol synthesis plant or gasoline synthesis plant.

REFERENCE SIGNS LIST

10 Regeneration column
20 Reboiler
40 Absorption column
100 Reformer
150 Methanol synthesis reaction apparatus
180 Distillation column
181 Reboiler
190 Carbon dioxide recovery apparatus

The invention claimed is:

1. A method for recovering carbon dioxide in a plant for synthesizing methanol from a hydrocarbon gas, the method comprising:
   a reforming step of producing a reformed gas by a steam reforming reaction of a hydrocarbon gas;
   a methanol synthesis step of synthesizing methanol from the reformed gas;
   a combustion step of combusting a fuel gas to obtain a heat source of the steam reforming reaction;
   a carbon dioxide recovery step of recovering carbon dioxide, using an absorption liquid, from a combustion exhaust gas generated by the combustion;
   a step of obtaining a plurality of reformed gas heating media or reformed gas and methanol heating media of different temperatures from the reformed gas, or the reformed gas and the methanol; and
   an absorption liquid regeneration step of regenerating the absorption liquid by heating stepwise the absorption liquid having carbon dioxide absorbed therein to remove carbon dioxide from the absorption liquid, the heating being performed utilizing the plurality of heating media of different temperatures in one absorption liquid regeneration apparatus.

2. The method according to claim 1, wherein
   at least a first heating medium of the plurality of heating media of different temperatures has a temperature of from 115 to 140° C., and a second heating medium has a temperature of from 90 to 110° C.

3. The method according to claim 1, further comprising a distillation step of distilling the methanol synthesized in the methanol synthesis step; wherein
   a heat exchange with the reformed gas generates an additional heating medium of different temperature, and the heating medium is used as a heat source of the distillation.

4. The method according to claim 1, further comprising a gasoline synthesis step of synthesizing gasoline from the methanol synthesized in the methanol synthesis step.

5. The method according to claim 1, wherein
   regeneration of the absorption liquid is performed by heating stepwise the absorption liquid having carbon dioxide absorbed therein, the heating being performed utilizing the plurality of reformed gases of different temperatures.

6. The method according to claim 1, wherein
   regeneration of the absorption liquid is performed by heating stepwise the absorption liquid having carbon dioxide absorbed therein, the heating being performed utilizing the reformed gases and methanol of different temperatures.

7. A system for recovering carbon dioxide and synthesizing methanol from a hydrocarbon gas, the system comprising:
   a reformer configured to produce a reformed gas by a steam reforming reaction of a hydrocarbon gas;
   a methanol synthesizing apparatus configured to synthesize methanol from the reformed gas;
   a combustion apparatus configured to combust fuel gas to obtain a heat source of the steam reforming reaction by the reformer;
   a carbon dioxide absorption apparatus configured to recover, using an absorption liquid, carbon dioxide from combustion exhaust gas generated by the combustion apparatus;
   a plurality of heat exchangers configured to use the reformed gas or the reformed gas and the methanol as a plurality of reformed gas heating media or reformed gas and methanol heating media of different temperatures; and
   one absorption liquid regeneration apparatus configured to regenerate the absorption liquid by heating stepwise the absorption liquid having carbon dioxide absorbed therein by the plurality of heat exchanges to remove carbon dioxide from the absorption liquid, the heating being performed utilizing the plurality of heating media of different temperatures in the one absorption liquid regeneration apparatus.

8. The system according to claim 7, wherein
   at least a first heating medium of the plurality of heating media of different temperatures has a temperature of from 115 to 140° C., and a second heating medium has a temperature of from 90 to 110° C.

9. The system according to claim 7, further comprising:
   a distillation apparatus configured to distill the methanol synthesized by the methanol synthesizing apparatus; and
   an additional heat exchanger configured to obtain an additional heating medium of different temperature by heat exchange with the reformed gas; wherein
   the additional heating medium of different temperature is used as a heat source of the distillation apparatus.

10. The system according to claim 7, further comprising a gasoline synthesizing apparatus configured to synthesize gasoline from the methanol synthesized by the methanol synthesis apparatus.

11. The system according to claim 7, wherein
    the plurality of heat exchangers are disposed so that the reformed gas and the absorption liquid having carbon dioxide absorbed therein are subjected to a plurality of heat exchanges stepwise.

12. The system according to claim 7, wherein
    at least a first heat exchanger of the plurality of heat exchangers is disposed so that the reformed gas and the absorption liquid having carbon dioxide absorbed therein are subjected to a heat exchange, and a second heat exchanger is disposed so that the methanol and the absorption liquid having carbon dioxide absorbed therein is subjected to a heat exchange.

13. The method according to claim 1, wherein the one absorption liquid regeneration apparatus comprises a bottom that collects the absorption liquid; and a chimney tray that collects down-flowing liquid while allowing rising gas to pass, wherein the method further comprises: extracting a first absorption liquid from the bottom of the one absorption liquid regeneration apparatus to heat the first extracted absorption liquid with one of the plurality of heating media of different temperatures; and extracting a second absorption liquid from the chimney tray of the one absorption liquid regeneration apparatus to heat the second extracted absorption liquid with another of the plurality of heating media of different temperatures.

14. The system according to claim 7, wherein the one absorption liquid regeneration apparatus comprises a bottom that collects the absorption liquid; and a chimney tray that collects down-flowing liquid while allowing rising gas to pass so that a first absorption liquid is extracted from the bottom to heat the first extracted absorption liquid with one of the plurality of heating media of different temperatures and a second absorption liquid is extracted from the chimney tray to heat the second extracted absorption liquid with another of the plurality of heating media of different temperatures.

* * * * *